United States Patent [19]

Brugmans et al.

[11] Patent Number: 4,584,305

[45] Date of Patent: Apr. 22, 1986

[54] AIDING THE REGRESSION OF NEOPLASTIC DISEASE WITH 2,3,5,6-TETRAHYDRO-6-PHENYLIMIDAZO[2,1-b]THIAZOLE

[75] Inventors: Josephus Brugmans, Schilde-Antwerp, Belgium; William Pollack, Belle Mead, N.J.; Paul A. J. Janssen, Vosselaar, Belgium; Daniel Tripodi, Westford, Mass.

[73] Assignee: Janssen Pharmaceutica N.V., Beerse, Belgium

[21] Appl. No.: 230,578

[22] Filed: Feb. 2, 1981

Related U.S. Application Data

[63] Continuation of Ser. No. 67,505, Aug. 17, 1979, abandoned, which is a continuation of Ser. No. 944,520, Sep. 30, 1978, abandoned, which is a continuation of Ser. No. 799,893, May 23, 1977, abandoned, which is a continuation of Ser. No. 591,795, Jun. 30, 1975, abandoned, which is a continuation-in-part of Ser. No. 424,030, Dec. 12, 1973, abandoned, which is a continuation-in-part of Ser. No. 281,367, Aug. 17, 1972, abandoned.

[51] Int. Cl.$^4$ ............................................ A61K 31/425
[52] U.S. Cl. .................................................... 514/368
[58] Field of Search ........................... 424/270; 514/368

[56] References Cited

PUBLICATIONS

Renoux et al., Nature, vol. 240, pp. 217–218 12-13-72.

*Primary Examiner*—Jerome D. Goldberg
*Attorney, Agent, or Firm*—Geoffrey G. Dellenbaugh

[57] ABSTRACT

Process of aiding regression and palliation of neoplastic disease in animal and human hosts comprising systemic administration to phenylimidazo[2,1-b]thiazole or a nontoxic acid addition salt thereof. Preferably the active ingredient is administered in a sufficient amount to provide dosages over the range from about 1 mg to about 5 mg/kg of body weight of the host.

17 Claims, No Drawings

AIDING THE REGRESSION OF NEOPLASTIC DISEASE WITH 2,3,5,6-TETRAHYDRO-6-PHENYLIMIDAZO[2,1-b]THIAZOLE

This is a continuation of application Ser. No. 067,505, filed Aug. 17, 1979, now abandoned, which in turn is a continuation of Application Ser. No. 944,520, filed Sept. 30, 1978, now abandoned, which in turn is a continuation of Application Ser. No. 799,893, filed May 23, 1977, now abandoned, which in turn is a continuation of Application Ser. No. 591,795, filed June 30,1975, now abandoned, which in turn is a continuation-in-part of Application Ser. No. 424,030, filed Dec. 12, 1973, now abandoned, which in turn is a continuation-in-part of Application Ser. No. 281,367, filed Aug. 17, 1972, now abandoned.

DESCRIPTION OF THE INVENTION

This invention relates to a process of ameliorating neoplastic disease in animal and human hosts. The essential active ingredient utilized in the process in an effective amount is 2,3,5,6-tetrahydro-6-phenylimidazo[2,1-b]thiazole (PIT). This compound is a well known anthelmintic, generically known as tetramisole in its racemic form and as levamisole in the form of the levo enantiomorph. From about 1 mg to about 5 mg/kg body weight of the host, calculated as the base form, is the preferred range for the essential ingredient.

PIT, in base form, may be readily converted to the corresponding therapeutically acceptable acid addition salt form by reaction with an appropriate inorganic acid, such as, for example, hydrochloric, hydrobromic, hydriodic, sulfuric, phosphoric and the like acids, or with an appropriate organic acid, such as, for example, acetic, propionic, glycolic, lactic, oxalic, malonic, tartaric, citric, sulfamic, ascorbic and the like acids. In turn, the salts of formula (I) may be converted to the corresponding base form by conventional treatment with suitable alkali. Of the acid addition salts, the hydrochloride is preferred.

Neoplastic disease, as used herein, is meant to include all types of cancerour growths or oncogenic processes, metastatic tissues or malignantly transformed cells, tissues, or organs, irrespective of histopathologic type or stage of invasiveness. For example, the subject compounds may be used in accordance with this invention against such neoplastic disorders as "Lewis Lung 3LL" tumor and pulmonary metastases, methylcholanthrene indeed sarcoma, Maloney leukemia, sarcoma 180 and the like in laboratory animals, for example, mice, and against such neoplastic disorders as shown in New-England J. Med., Vol. 289, P. 354 (1973).

The process of this invention comprises systemically administering to subjects hosting neoplastic disease an effective ameliorating amount of PIT or a therapeutically active acid addition salt thereof preferably admixed with a pharmaceutically acceptable carrier. Such carrier may take a wide variety of forms depending on the form of preparation desired for administration, i.e., oral or parenteral. In preparing the compositions in oral dosage form, any of the usual pharmaceutical media may be employed, such as, for example, water, glycols, oils, alcohols, and the like in the case of oral liquid preparations such as suspensions, elixirs and solutions or solid carriers such as starches, sugars, kaolin, lubricants, binders, disintegrating agents and the like in the case of powders, capsules and tablets. Because of their case in administration, tablets and capsules represents the most advantageous oral dosage form, in which case solid pharmaceutical carriers are obviously employed. For parenteral injection, the carrier will usually comprise sterile water, at least in large part, though other ingredients, for example, to aid solubility, may be included. Injectable solutions, for example may be prepared in which the carrier comprises saline solution, glucose, solution or a ixture of saline and glucose solution. Injectable suspensions may also be prepared in which case appropriate liquid carriers, suspending agents and the like may be employed.

It is especially advantageous to formulate the aforementioned pharmaceutical compositions in dosage unit form for ease of administration and uniformity of dosage. Dosage unit form, as used herein, refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonfuls, tablespoonfuls and the like, and segregated multiples thereof. The amount of active ingredient per dosage unit may range from about 5 mg to about 500 mg, and, preferably, from about 50 mg to about 250 mg.

The dosage of the principal active ingredient (PIT) for the treatment of the particular neoplastic disease may depend on the species and size of the subject being treated; the particular condition and its severity; the particular form of the active ingredient (e.g., soluble salt or less soluble base) and the route of administration. In any case the dose to be used is one nontoxic to the recipient. In general, a dose of from about 1.0 mg/kg body weight up to the nontoxic anthelmintic dose for the particular host can be generally utilized for the treatment of neoplastic disease well. For example, the recommended nontoxic anthelmintic oral dose for tetramisole is about 5 mg/kg in man, about 15 mg/kg in sheep, about 10 mg/kg in cattle, and about 40 mg/kg in chickens; and for levamisole about 2.5 mg/kg in man, about 8 mg/kg in sheep, and about 8 mg/kg in cattle. Expressed as amounts suited for single unit doses, from about 5 to about 500 mg is operable and expedient for most subjects.

In humans, a dose of from about 1.0 mg/kg to about 5 mg/kg, or a daily total dose or from about 50 to about 500 mg given singly or in divided doses embraces the effective range for the treatment of most neoplastic diseases.

Regression and palliation of neoplastic disease are aided by the internal administration of PIT, preferably as the hydrochloride salt of the levo enantiomorph, and pharmaceutical compositions containing same.

As a dosage regimen, the amount of principal active ingredient administered is a sufficient amount to aid regression and palliation of the neoplastic disease in the absence of excessive deleterious side effects of a cytotoxic nature to the host harboring the disease. Specific modes of administration are 150 mg/kg of levamisole or 250–300 mg/kg of tetramisole daily to humans for about 3 to 5 days repeated every 2–3 weeks. In certain instance, continuous daily administration of 100–200 mg/kg of levamisole or 200–300 mg/kg of tetramisole may be maintained over a long period of time, for example 3–6 months.

EXAMPLE I

Injectable solution: A sterile aqueous solution suitable for intramuscular or intravenous use, and containing 250 mg or tetramisole hydrochloride as the active ingredient (A.I.) in each ml, is prepared from the following formulation:

| | |
|---|---|
| Tetramisole HCl | 250 gms |
| Water for Injection, U.S.P., q.s. ad | 1,000 ml |

EXAMPLE II

Capsules: 10,000 Hard gelatin capsules, each containing as the active ingredient 150 mg of levamisole hydrochloride, are prepared from the following formulation:

| | Grams |
|---|---|
| Levamisole HCl | 1,500 |
| Lactose | 500 |
| Starch | 150 |
| Talc | 150 |
| Calcium Stearate | 10 |

A uniform mixture of the active and supplementary ingredients is prepared and filled into two-piece hard gelatin capsules. The capsules provide satisfactory regression and palliation of neoplastic disease in adults with a regimen of 1 capsule given daily for 3 days, said regimen being repeated every three weeks.

EXAMPLE III

Tablets: 5,000 Compressed tablets, each containing as the active ingredient 150 mg of levamisole hydrochloride, are prepared from the following formulation:

| | Grams |
|---|---|
| Levamisole HCl | 750 |
| Starch | 75 |
| Dibasic calcium phosphate hydrous | 325 |
| Calcium stearate | 3.5 |

The finely powdered ingredients are mixed well and granulated with 10% starch paste. The granulation is dried and compressed into tablets. The oral administration of one tablet a day for 3 days, repeated every 3 weeks, provides satisfactory regression and palliation of neoplastic disease in adult human. The tablets may be sugar coated to mask the tast of the active ingredient.

EXAMPLE IV

The following formulation provides 5 liters of an oral suspension comprising 50 mg of di-2,3,5,6-tetrahydro-6-phenylimidazo[2,1-b]thiazole as the active ingredient (A.I.) per teaspoonful (5 mls):

| | Grams |
|---|---|
| A.I. | 25.0 |
| Sucrose | 300.0 |
| Dioctyl sodium sulfosuccina | 0.5 |
| Bentonite | 22.5 |
| Methyl paraben | 7.5 |

-continued

| | Grams |
|---|---|
| Propyl paraben | 1.5 |
| Antifoam A.F. Emulsion | 0.15 |
| Propylene glycol | 52.0 |
| FD & C Yellow #5 | 0.1 |
| Sodium cyclamate | 50.0 |
| Sodium saccharin | 5.0 |
| Orange flavor | 7.5 |
| Filtered purified water, q.s., ad | 5 liters |

Dissolve the parabens in the propylene glycol and add this solution to a solution of the sodium cyclamate, sodium saccharin and sucrose in half the water. Suspend the bentonite in hot (about 85° C.) water and stir for 60 minutes. Add the bentonite solution to the former solution.

Dissolve the sulfosuccinate in some water and suspend the A.I. in the resulting solution. Add the Antifoam A.F. Emulsion which had been diluted to a lotion consistency with a minimum amount of water and mix well.

Add the letter suspension of A.I. to the former mixture and mix well. Add the FD&C Yellow #5 dissolved in a small amount of water. Add the orange flavor, q.s. to volume with water, and stir to a homogeneous mixture. Pass the mixture through a colloid mill and fill into suitable containers.

EXAMPLE V

Two-month-old female C57Bl/Rho mice were inoculated subcutaneously in the flank with 0.2 ml. of a tumor cell suspension that contained $2.5 \times 10^6$ live cells (trypan blue exclusion test) per ml. Three weeks later all mice were killed, the primary subcutaneous tumor excised and weighed, and the lungs examined for metastases that appeared as white nodules against the black substance of normal lung tissue following injection of dilute India ink through the trachea before fixation of the whole lung.

In our experiment, all mice were inoculated on the same day with $5 \times 10^5$ live tumor cells suspended in buffered saline, pH 7.2 (Table 1). After 24 hr one group of mice taken at random was treated by a single subcutaneous injection of 0.1 ml. of levamisole dissolved in sterile pyrogen-free saline (0.5 mg kg$^{-1}$. In a second randomized group treatment by levamisole, 0.5 mg kg$^{-1}$ at each injection, was started 7 days after tumour inoculation when palpable tumor nodules had already developed in all untreated mice. Levamisole treatment in this group was continued every 2 days up to the 17th day, for a total of 6 injections. Controls were left untreated (Table 1).

Findings at autopsies on day 21 after tumo inoculation were statistically analyzed. Table 1 shows that a single injection of 0.5 mg kg$^{-1}$ of levamisole sufficed to completely cure 3 out of 12 mice and significantly (P=0.01) inhibited both the primary tumor growth and the number of pulmonary metastases in the 9 other mice of that group. Levamisole treatment also cured 4 out of 10 mice when treatment was started after subcutaneous tumor had developed. In the same group of mice, one additional animal did not demonstrate any lung metastases. Primary tumor and pulmonary metastases were significantly (P=0.01) reduced in the remaining mice of that group.

TABLE 1

| | | | Primary tumour | | | Lung metastases | | |
|---|---|---|---|---|---|---|---|---|
| Group No. | Treatment | No. of mice | Negative intake | Geometric mean weight (g) in positive mice | Confidence interval (0.95) | Negative mice | Geometric mean No. in positive mice | Confidence interval (0.95) |
| 1 | None | 10 | 0 | 3.70 | (3.39–4.01) | 0 | 20.2 | (18.2–22.4) |
| 2 | 0.5 mg kg$^{-1}$ levamisole, day 1 | 12 | 3 | 2.27 | (1.43–3.11) ⎫ NS | 3 | 3.2 ⎫ NS | (0.7–5.7) |
| 3 | 0.5 mg kg$^{-1}$ levamisole, days 7, 9, 11, 13, 15, 17 | 10 | 4 | 1.40 | (0.93–1.87) ⎭ | 5 | 3.0 ⎭ | (1.5–4.5) |

Table 1: Levamisole Activity on the Primary 3 LL Tumour and Pulmonary Metastases The foregoing example demonstrates the activity of levamisole, a simple chemical compound devoid of toxicity (mouse LD$_{50}$=121 mg/kg), against the growth of primary subcutaneous 3 LL tumor and against the development of pulmonary metastases.

What is claimed is:

1. A process of aiding regression and palliation of neoplastic disease which comprises the systemic administration to human and animal subjects hosting the neoplastic disease of an effective anti-neoplastic amount of a member selected from the group consisting of 2,3,5,6-tetrahydo-6-phenylimidazo[2,1-b]thiazole and the therapeutically active acid addition salts thereof in a pharmaceutical carrier.

2. A process of aiding regression and palliation of neoplastic disease which comprises the systemic administration to a human hosting the neoplastic disease of from about 1 to about 5 mg/kg body weight of the host of a member selected from the group consisting of 2,3,5,6-tetrahydro-6-phenylimidazo[2,1-b]thiazole and the therapeutically active acid addition salts thereof.

3. A process of aiding regression and palliation of pulmonary metastatic tumor which comprises the systemic adminstration to a host of said tumor of an effective tumor-inhibiting amount of a member selected from the group consisting of 2,3,5,6-tetrahydro-6-phenylimidazo[2,1-b]thiazole and the therapeutically active acid addition salts thereof in a pharmaceutical carrier.

4. A process of aiding regression palliation of breast cancer which comprises the systemic administration to human or animal subjects hosting breast cancer of an effective antineoplastic amount of a member selected from the group consisting of 2,3,5,6-tetrahydro-6-phenylimidazo[2,1-b]thiazole and the therapeutically active acid addition salts thereof in a pharmaceutical carrier.

5. A process of aiding regression and palliation of breast cancer which comprises the systemic administration to a human hosting breast cancer of from about 1 to about 5 mg/kg body weight of the host of a member selected from the group consisting of 2,3,5,6-tetrahydro-6-phenylimidazo-[2,1-b]thiazole and the therapeutically active acid addition salts thereof.

6. A process of aiding regression and palliation of lung cancer which comprises the systemic administration to human or animal subjects hosting lung cancer of an effective antineoplastic amount of a member selected from the group consisting of 2,3,5,6-tetrahydro-6-phenylimidazo[2,1-b]thiazole and the therapeutically active acid addition salts thereof in a pharmaceutical carrier.

7. A process of aiding regression and palliation of lung cancer which comprises the systemic administration to a human hosting lung cancer of from about 1 to about 5 mg/kg body weight of the host of a member selected from the group consisting of 2,3,5,6-tetrahydro-6-phenylimidazo[2,1-b]thiazole and the therapeutically active acid addition salts thereof.

8. A process of aiding regression and palliation of malignant melanoma which comprises the systemic administration to human or animal subjects hosting malignant melanoma of an effective antineoplastic amount of a member from the group consisting of 2,3,5,6-tetrahydro-6-phenylimidazo[1,2-b]thiazole and the therapeutically active acid addition salts thereof in a pharmaceutical carrier.

9. A process of aiding regression and palliation of malignant melanoma which comprises the systemic administration to a human hosting malignant melanoma of from about 1 to about 5 mg/kg body weight of the host member selected from the group consisting of 2,3,5,6-tetrahydro-6-phenylimidazo[2,1-b]thiazole and the therapeutically active acid addition salts thereof.

10. A process of aiding regression and palliation of colorectal cancer which comprises the systemic administration to human or animal subject hosting colorectal cancer of an effective antineoplastic amount of a member selected from the group consisting of 2,3,5,6-tetrahydro-6-phenylimidazo-[2,1-b]thiazole and the therapeutically active acid addition salts thereof in a pharmaceutical carrier.

11. A process of aiding regression and palliation of colorectal cancer which comprises the systemic administration to a human hosting colorectal cancer of from about 1 to about 5 mg/kg body weight of the host of a member selected from the group consisting of 2,3,5,6-tetrahydro-6-phenylimidazo-[2,1-b]thiazole and the therapeutically active acid addition salts thereof.

12. A process of aiding regression and palliation of multiple myeloma which comprises the systemic administration to human or animal subjects hosting multiple myeloma of an effective antineoplastic amount of a memeber selected from the group consisting of 2,3,5,6-tetrahydro-6-phenylimidazo-[2,1-b]thiazole and the therapeutically active acid addition salts thereof in a pharmaceutical carrier.

13. A process of aiding regression and palliation of multiple myeloma which comprises the systemic administration to a human hosting multiple myeloma of from about 1 to about 5 mg/kg body weight of the host of a member selected from the group consisting of 2,3,5,6-tetrahydro-6-phenylimidazo-[2,1-b]thiazole and the therapeutcially active acid addition salts thereof.

14. A process of aiding regression and palliation of head and neck cancer which comprises the systemic administration to human or animal subjects hosting head and neck cancer of an effective antineoplastic amount of a member selected from the group consisting of 2,3,5,6-tetrahydro-6-phenylimidazo-[2,1-b]thiazole and the therapeutically active acid addition salts thereof in a pharmaceutical carrier.

15. A process of aiding regression and palliation of head and neck cancer which comprises the systemic administration to a human hosting head and neck cancer of from about 1 to about 5 mg/kg body weight of the host of a member selected from the group consisting of 2,3,5,6-tetrahydro-6-phenylimidazo-[2,1-b]thiazole and the therapeutically active acid addition salts thereof.

16. A process of aiding regression and palliation of gastric cancer which comprises the systemic administration to human and animal subjects hosting gastric cancer of an effective antineoplastic amount of a member selected from the group consisting of 2,3,5,6-tetrahydro-6-phenylimidazo-[2,1-b]thiazole and the therapeutically active acid addition salts thereof in a pharmaceutical carrier.

17. A process of aiding regression and palliation of gastric cancer which comprises the systemic administration to a human hosting gastric cancer of from about 1 to about 5 mg/kg body weight of the host of a member selected from the group consisting of 2,3,5,6-tetrahydro-6-phenylimidazo-[2,1-b]thiazole and the therapeutically active acid addition salts thereof.

* * * * *

UNITED STATES PATENT AND TRADEMARK OFFICE
CERTIFICATE OF CORRECTION

PATENT NO. : 4,584,305
DATED : April 22, 1986
INVENTOR(S) : Brugmans et al.

It is certified that error appears in the above-identified patent and that said Letters Patent is hereby corrected as shown below:

Claim 4, line 43 delete "regression palliation" and insert -- regression and palliation --.

Claim 8, line 21 delete "[1,2-b] and insert --[2,1-b] --.

Claim 12, line 50 delete "memeber" and insert -- member --.

Signed and Sealed this

Thirtieth Day of September 1986

[SEAL]

Attest:

DONALD J. QUIGG

Attesting Officer

Commissioner of Patents and Trademarks

UNITED STATES PATENT AND TRADEMARK OFFICE

CERTIFICATE EXTENDING PATENT TERM
UNDER 35 U.S.C. 156

Patent No.      : 4,584,305

Dated           : April 22, 1986

Inventor(s)     : Josephus Brugmans et al.

Patent Owner    : Janssen Pharmaceutica N.V.

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

423 DAYS with all rights pertaining thereto as provided by 35 U.S.C. 156 (b).

I have caused the seal of the Patent and Trademark Office to be affixed this 25th day of July, 1991.

Harry F. Manbeck, Jr.
Assistant Secretary and Commissioner
of Patents and Trademarks